US007011653B2

(12) United States Patent
Imsangjan et al.

(10) Patent No.: US 7,011,653 B2
(45) Date of Patent: Mar. 14, 2006

(54) ABSORBENT PANT GARMENTS HAVING HIGH LEG CUTS

(75) Inventors: W. Ann Imsangjan, Neenah, WI (US); Michael Donald Sperl, Waupaca, WI (US); Christopher Peter Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 347 days.

(21) Appl. No.: 10/165,185

(22) Filed: Jun. 7, 2002

(65) Prior Publication Data

US 2003/0229327 A1 Dec. 11, 2003

(51) Int. Cl.
*A61F 13/15* (2006.01)
(52) U.S. Cl. .............................. 604/385.01; 604/385.3
(58) Field of Classification Search ........... 604/385.01, 604/385.21–385.3
See application file for complete search history.

(56) References Cited

U.S. PATENT DOCUMENTS

| | | | |
|---|---|---|---|
| 4,940,464 A | | 7/1990 | Van Gompel et al. |
| 5,853,405 A | * | 12/1998 | Suprise ........................ 604/391 |
| 5,910,224 A | | 6/1999 | Morman |
| 5,931,827 A | | 8/1999 | Buell et al. .............. 604/385.2 |
| 6,049,916 A | * | 4/2000 | Rajala et al. ................... 2/400 |
| 6,443,940 B1 | * | 9/2002 | Ashton et al. ............... 604/396 |
| 6,524,293 B1 | | 2/2003 | Elsberg et al. ......... 604/385.13 |
| 6,579,275 B1 | | 6/2003 | Pozniak et al. ............. 604/390 |
| 2002/0112276 A1 | | 8/2002 | Ruman et al. .................. 2/400 |
| 2002/0173768 A1 | | 11/2002 | Elsberg et al. .............. 604/391 |

FOREIGN PATENT DOCUMENTS

| | | |
|---|---|---|
| JP | 9-66071 | 3/1997 |
| WO | 00/35399 | 6/2000 |
| WO | 00/37009 | 6/2000 |
| WO | WO 02/36060 | 5/2002 |

* cited by examiner

*Primary Examiner*—Tatyana Zalukaeva
*Assistant Examiner*—C. Lynne Anderson
(74) *Attorney, Agent, or Firm*—Pauley Petersen & Erickson

(57) ABSTRACT

An absorbent pant garment having high leg cuts. The garment includes an absorbent chassis defining a waist opening and a pair of leg openings. The absorbent chassis includes a front region, a crotch region, a back region, two side panels connecting the front region and the back region. The side panels may include refastenable side seams between front and back panels, a permanently bonded side seam, or no side seams at all. In embodiments having refastenably attached side panels, the front side panels may have an S shape along a bottom edge to minimize the possibility of a pointed piece of the back side panels sticking out. The high-cut side regions may be defined by a ratio of side panel width at a narrowest longitudinal dimension of the side panel divided by a width of the side panel along a side seam of less than about 0.7. Alternatively, the high-cut side regions may be defined by a ratio of leg opening circumference divided by waist opening circumference of at least about 0.7.

22 Claims, 9 Drawing Sheets

ABSORBENT PANT GARMENTS HAVING HIGH LEG CUTS

BACKGROUND OF THE INVENTION

This invention is directed to absorbent pant garments having leg openings cut in such a way that the side regions of the garments are longitudinally narrow and sit substantially above a wearer's thighs.

Absorbent pant garments typically include a pair of side panels that extend from a waist opening to a leg opening, covering a wearer's hips and an upper portion of the wearer's outer thigh area. This full side panel design originated as an effort to reduce leakage. As other features of absorbent pant garments have evolved, these full, or low-cut, side panels have remained relatively consistent in size and shape. For instance, absorbent pant garments used to be relatively loose, with close adherence to the wearer around the waist opening and the leg openings. As these garments have evolved into more close-fitting garments, donning and doffing the garments has become increasingly difficult for wearers, due to increased frictional forces.

While such full side panels may indeed reduce leakage, additional features have also been found to reduce leakage. Elastomeric materials used to be more prone to stress relaxation over time, such as overnight, especially at body temperature, compared to current elastomeric materials. Thus, due to advances in elastomeric technology, absorbent technology, and the advent of additional disposable absorbent garment features, leakage reduction may be provided in absorbent pant garments without the necessity of full, or low-cut, side panels.

Full side panels, while effective in reducing leakage, may present a number of drawbacks for wearers. With the side panels extending over a portion of a wearer's outer thigh area, the side panel coverage may hinder the wearer's movements and cause general discomfort and possibly skin irritation. Also, this extent of coverage causes the garment to move in response to the wearer's slightest leg movements, which may cause an indiscreet rustling sound often associated with disposable absorbent garments, as well as possible gapping around the leg openings. Furthermore, the bulk of such long side panels makes it difficult to camouflage the presence of such garments beneath clothing, and also makes donning and doffing the garment more challenging. Additionally, low-cut side panels create relatively small leg openings, which can be difficult for children to get their feet through the small holes. The size of the leg opening could be increased by using back side panels that are cut high, but this has deleterious side effects in that the product looks less like underwear because too much of the buttocks are exposed. A high cut back side panel that is similar in size and shape to the front panel also makes it difficult to tell the front from the back of a pant, especially for children. Donning a disposable absorbent pant backwards can be a problem because most absorbent pants are designed with a majority of the absorbent material in the front. An absorbent pant that is worn backwards is usually more prone to leak if a child wets in it.

One drawback associated with full, or low-cut, side panels as well as with narrower, or high-cut, side panels is that absorbent pant garments having refastenable side seams integrated within low-cut or high-cut side panels often have sharp corners at the leg edges of the refastenable side seams. Typically the refastenable side seams are designed in such a way that a front side panel can be refastenably attached to a back side panel with one of the side panels overlapping the other such that, if carefully aligned, no sharp edges stick out from the refastenable seam. However, due to process variability and user fastening variability, sharp edges may end up sticking out from the refastenable seams, resulting in skin irritation to the wearer. Furthermore, these protruding corners are where "pop-opens" of the seam are typically initiated. Additionally, these protruding corners are tempting for children to pick at, thus resulting in a child unintentionally opening the side seam. Also, protruding corners may result in a non-underwear-like appearance of the garment and may give the perception of poor quality.

There is a need or desire for absorbent pant garments that are more "underwear-like" in terms of comfort, discreetness, and ease of use, without sacrificing leakage protection. There is also a need or desire for a refastenable side seam design for absorbent pant garments that is more tolerant to process and user fastening variability, and prevents any sharp corners of the side panels from protruding from the seam.

SUMMARY OF THE INVENTION

In response to the discussed difficulties and problems encountered in the prior art, a new, underwear-like, absorbent pant garment has been discovered. This absorbent pant garment has high-cut side panels, such that the side panels are considerably narrower in a longitudinal direction compared to side panels in conventional absorbent pant garments. The absorbent pant garment may include refastenable side seams that prevent any sharp corners of the side panels from protruding from the seam.

The absorbent pant garments of the invention include an absorbent chassis that defines a waist opening and a pair of leg openings. The absorbent chassis has a front region and a back region with a crotch region between the front and back regions. A pair of side panels also joins the front region and the back region on opposite transverse sides of the garment. The side panels taper in longitudinal dimension to a narrowest longitudinal dimension at some point between the front region and the back region. In one embodiment, each of the side panels has a ratio of side panel width at the narrowest longitudinal dimension versus the width of the side panel along a side seam of less than or equal to 0.7. This ratio may be less than about 0.6, or less than about 0.5. In other embodiments, particularly those in which the side panels are integral with the front and back regions thereby lacking any attachment seams with the front region, the high-cut side panel may be defined by a ratio of the leg circumference divided by the waist circumference of at least about 0.7. This ratio may be at least about 0.8, or at least about 0.9.

The side panels of the absorbent pant garments may each be one-piece panels, or two or more pieces permanently bonded to one another forming at least one side seam between the front and back regions. The narrowest longitudinal dimension of the side panels is suitably located on a front side panel, or may be located roughly mid-way between the front and back regions.

In other embodiments, the side panels may each include two or more pieces releasably engageable with one another through the application of a releasably engageable fastening system. In particular, the side panels may each include a front panel and a back panel, releasably engageable with one another. The front panel may overlap the back panel, or vice-versa. Additionally, the front panel may have an S shape along a bottom edge to minimize any sharp corners at the leg opening that can result when a lap seam is formed. This S shape is particularly advantageous in designs having a higher leg cut since the high-cut leg opening necessitates a relatively highly angled shape in the back panels. The S shape effectively covers the angled corner of the back panel, thereby minimizing or softening any corners that result from process and/or user fastening variability. Suitably, in one embodiment in which the front panel has an S-shaped bottom edge, the narrowest longitudinal dimension of the front panel is narrower than the narrowest longitudinal dimension of the back panel.

The absorbent chassis suitably includes an outer cover that covers the front region, crotch region, and back region. In certain embodiments, the outer cover may also cover the side panels as well, creating an all-encompassing, one-piece garment exterior. Any suitable materials may be used to make the outer cover, such as stretchable or elastomeric materials. The garments may also include an absorbent pad in the crotch region that is contoured to fit within the shape of a stretchable or elastomeric outer cover.

With the high-cut side panels, the garments of the invention are designed to apply more pressure in a localized area to the body, thereby generating greater friction against the skin to hold the garment up. The localized pressures may tip the balance of frictional forces to favor the garments staying up when an outer garment, such as an undergarment, is pulled down. Greater friction between the garments of the invention and the wearer's body can overcome the friction between the garments and any outer garments that could otherwise pull the product down. Also, the garments may be easier to pull up compared to conventional absorbent pant garments, since the high-cut side panels produce less drag against the wearer's legs.

The resulting absorbent pant garments of the invention provide a more secure, form-fitting product, compared to conventional absorbent pant garments, and have a styled appearance. In addition to providing these benefits, the high-cut side panels also provide an unprecedented level of discreetness, both in terms of less bulk as well as a reduction in the rustling and crinkling noises normally associated with absorbent pant garments. Furthermore, the high-cut side panels lie predominantly over low-motion areas of the body, i.e. the hips rather than the hips and thighs, thus reducing the likelihood of gapping when the wearer is in an unusual position or during extreme motions.

With the foregoing in mind, it is a feature and advantage of the invention to provide an absorbent pant garment with high-cut side panels and having the comfort and style of underwear, with the absorbent and containment properties of a conventional absorbent pant garment.

BRIEF DESCRIPTION OF THE DRAWINGS

These and other objects and features of this invention will be better understood from the following detailed description taken in conjunction with the drawings, wherein.

Definitions

Within the context of this specification, each term or phrase below will include the following meaning or meanings.

"Absorbent pant product" includes diapers, diaper pants, training pants, swim wear, absorbent underpants, adult incontinence products, feminine hygiene products, and the like. The term "disposable garment" includes garments that are typically disposed of after 1–5 uses.

"Attached" refers to the joining, adhering, connecting, bonding, or the like, either permanently or temporarily, of at least two elements. Two elements will be considered to be attached together when they are attached directly to one another or indirectly to one another, such as when each is directly attached to intermediate elements.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Layer" when used in the singular can have the dual meaning of a single element or a plurality of elements.

Figure 3:
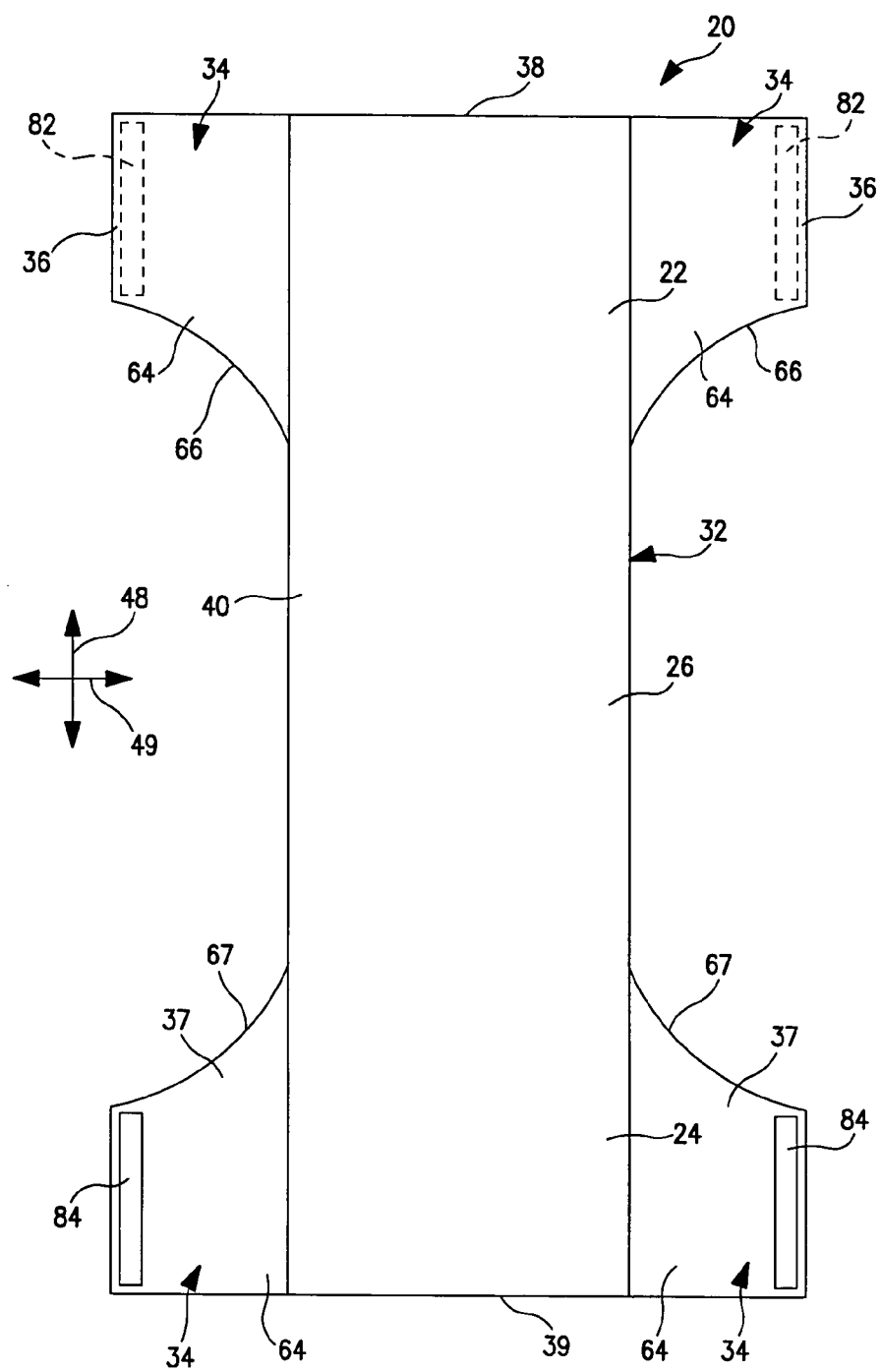
FIG. 3 plan view of a representative absorbent pant garment of the invention in a partially disassembled, stretched flat state, and showing the surface of the garment that faces away from the wearer when the article is worn.
Figure 4:
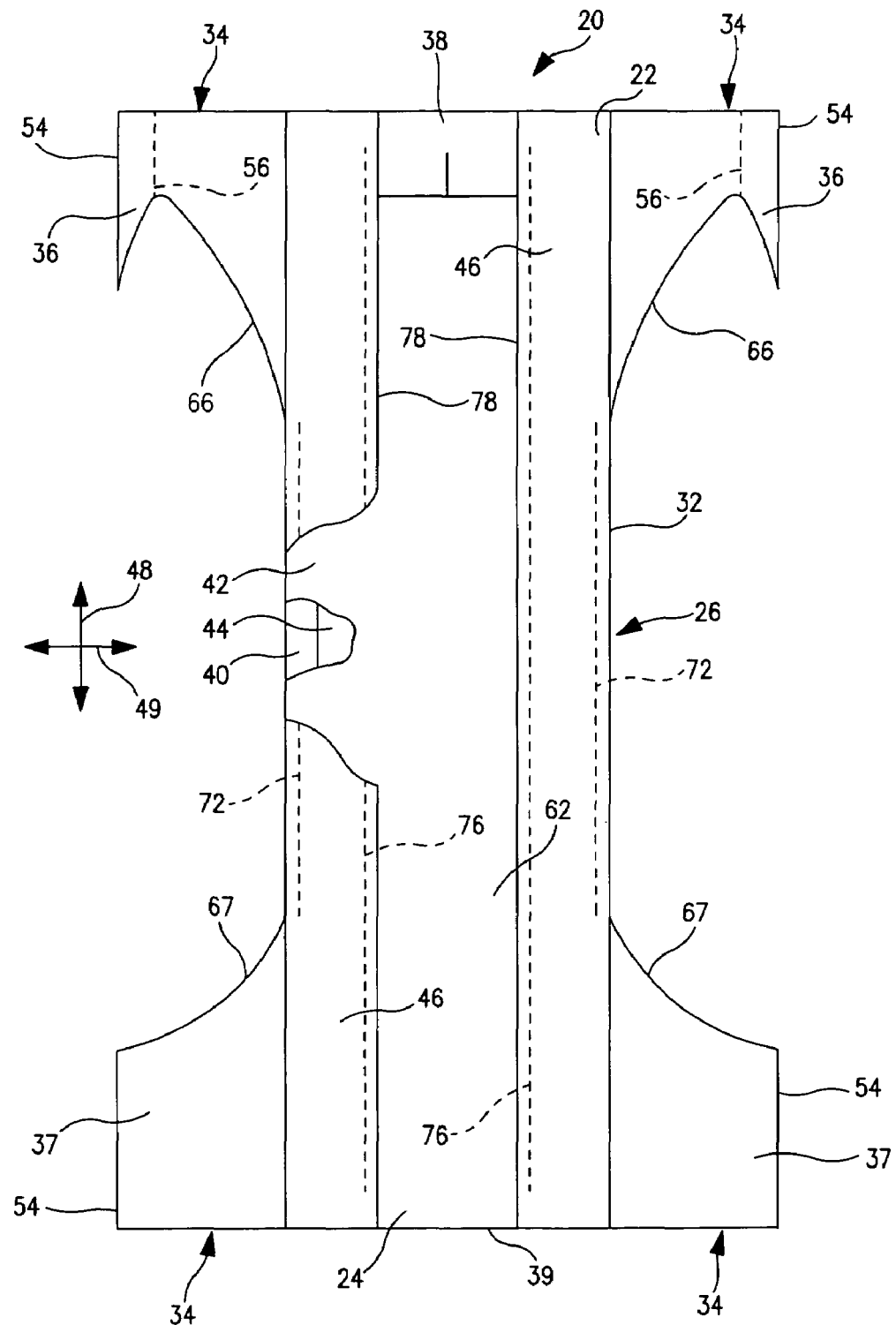
FIG. 4 is a plan view of a representative absorbent pant garment of the invention in a partially disassembled, stretched flat state, and showing the surface of the garment that faces the wearer when the article is worn, and with portions cut away to show underlying features.

"Longitudinal" and "transverse" have their customary meaning, as indicated by the longitudinal and transverse axes depicted in FIGS. 3 and 4. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Necked" refers to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions.

"Nonwoven" or "nonwoven web" refers to materials and webs of material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Permanently attached" or "permanently bonded" refers to the joining, adhering, connecting, attaching, bonding, or the like, of two elements of an absorbent garment such that the elements tend to be and remain attached during normal use conditions of the absorbent garment.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

DESCRIPTION OF PREFERRED EMBODIMENTS

The present invention is directed to absorbent pant garments having high-cut side panels, such that the side panels are considerably narrower in a longitudinal direction compared to side panels in conventional absorbent pant garments. Consequently, the absorbent pant garments of the invention resemble underwear in terms of comfort and discreetness, with the added feature of absorbent capacity.

The principles of the present invention can be incorporated into any suitable disposable absorbent pant garment. Examples of such suitable garments include diapers, diaper pants, training pants, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Figure 1:
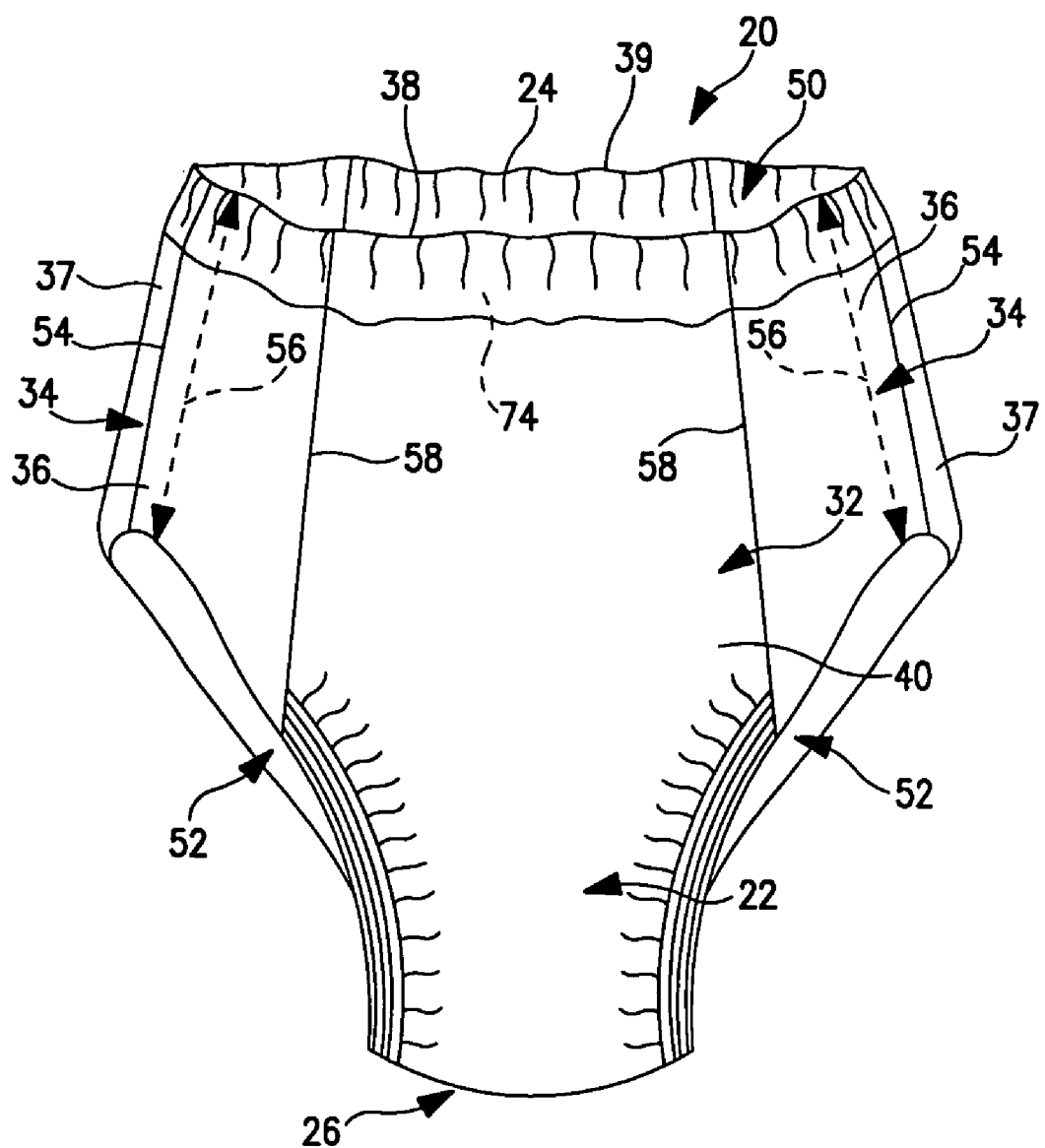
FIG. 1 is a front perspective view of a representative absorbent pant garment of the invention.

Referring to FIG. 1, a training pant 20 having high-cut side panels 34 is illustrated. The training pant 20 includes a chassis 32 defining a front region 22, a back region 24, and a crotch region 26 interconnecting the front and back regions. The chassis 32 also includes a pair of high-cut side panels 34, or side regions, interconnecting the front and back regions. The chassis 32 includes a body side liner 42 which is configured to contact the wearer, and an outer cover 40 opposite the body side liner which is configured to contact the wearer's clothing. An absorbent assembly 44 (FIG. 4) is positioned or located between the outer cover 40 and the body side liner 42.

Figure 2:
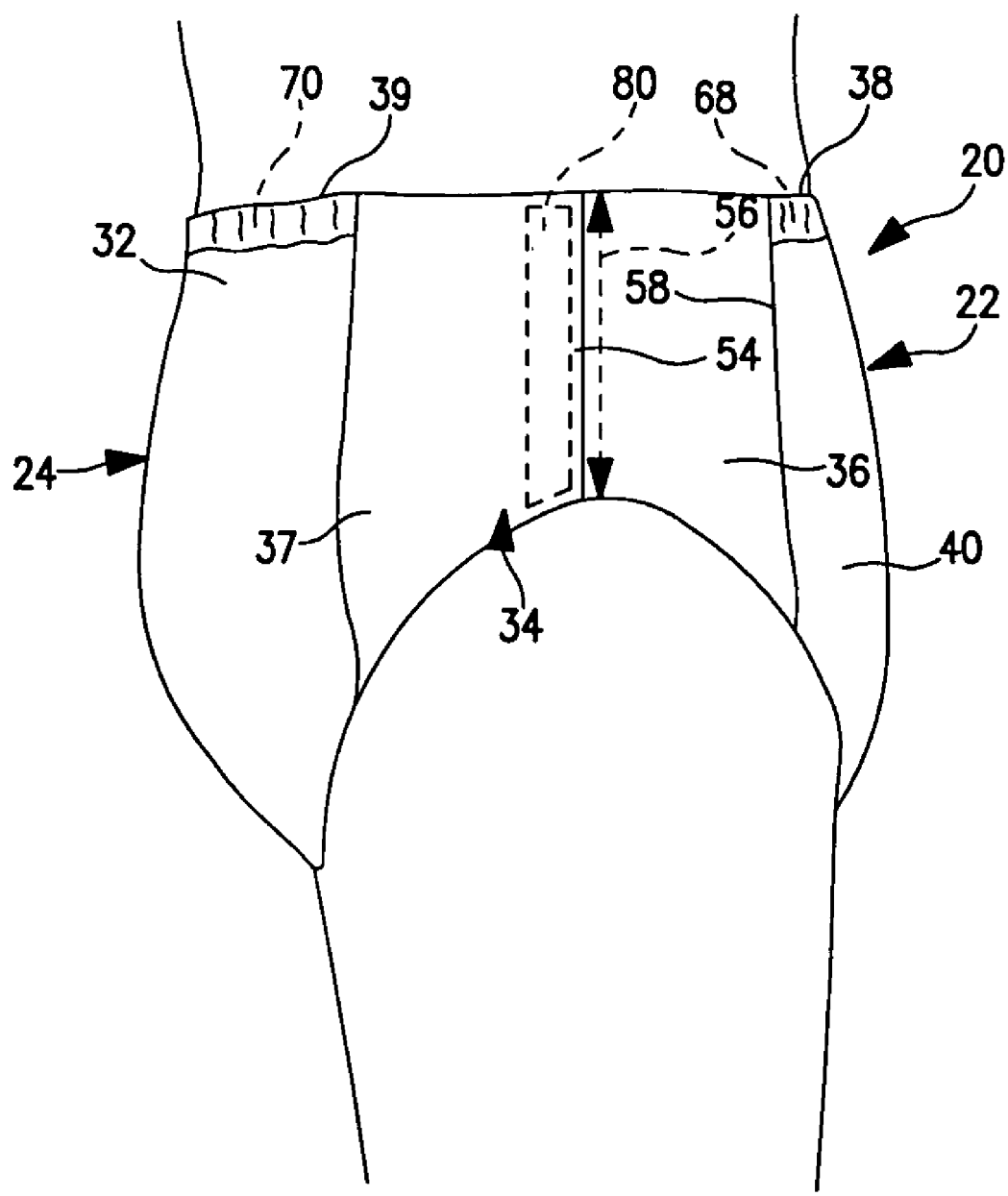
FIG. 2 is a side perspective view of another representative absorbent pant garment of the invention on a wearer.

FIG. 2 illustrates a training pant 20, similar to the training pant 20 illustrated in FIG. 1 but having refastenable sides. A training pant 20 having permanently bonded sides, as shown in FIG. 1, or a training pant 20 having refastenable sides in the fastened position, as shown in FIG. 2, defines a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer.

As shown in further detail in FIGS. 3 and 4, the chassis 32 also defines a pair of longitudinally opposed waist edges, which are designated front waist edge 38 and back waist edge 39. The front region 22 is contiguous with the front waist edge 38, and the back region 24 is contiguous with the back waist edge 39. An elastic waistband may partially or fully encircle the garment along the front and back waist edges 38, 39. For reference, arrows 48 and 49 depicting the orientation of the longitudinal axis and the transverse axis, respectively, of the training pant 20 are illustrated in FIGS. 3 and 4.

The illustrated absorbent chassis 32 includes a pair of transversely opposed side panels 34. The side panels 34 may each be one-piece panels, or two or more pieces permanently bonded to one another forming at least one side seam 54 between the front and back regions 22, 24. The side panels 34, whether they include one or multiple pieces, are attached to both the front region 22 and the back region 24 of the training pant 20. In another embodiment, the side panels 34 may be integral with the front and back regions 22, 24, thereby lacking any attachment seams with the front region 22 and the back region 24. In any case, the side panels 34 taper in longitudinal dimension to a narrowest longitudinal dimension 56 at some point or for some distance between the front region 22 and the back region 24. In one embodiment, each of the side panels 34 has a ratio of side panel width at the narrowest longitudinal dimension 56 divided by the width of the side panel along the side seam 54 of less than about 0.7. This ratio may be less than about 0.6, or less than about 0.5. The side seam 54 is where a front panel of the side panel 34 is attached to a back panel of the same side panel 34. The measurements for the side panel width at the narrowest longitudinal dimension 56 and the width of the side panel along the side seam 54 are measured according to the side panel dimensions measurement procedure described in detail below.

Alternatively, the high-cut side region 34 may instead be defined by a ratio of the leg circumference divided by the waist circumference of at least about 0.7. This ratio may be at least about 0.8, or at least about 0.9. The leg and waist circumferences are measured according to the circumference measurement procedure described in detail below. In particular, the waistband and leg section circumferences are measured at a force of 70 grams.

In other embodiments, the side panels 34 may each include two or more pieces releasably engageable with one another through the application of a releasably engageable fastening system 80. In particular, the side panels 34 may each include a front panel 36 attached to the front region 22 and a back panel 37 attached to the back region 24, the front and back panels 36, 37 being releasably engageable with one another. Alternatively, the front panels 36 may be integrally formed with the front region 22 and the back panels 37 may be integrally formed with the back region 24, while the front panels 36 and back panels 37 remain releasably engageable with one another.

The fastening system 80 may include fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. In one embodiment, the outer cover material and/or the body side liner material may serve as a loop type fastener.

Hook type fasteners typically include a fabric or material having a base or backing structure and a plurality of hook members extending upwardly from at least one surface of the backing structure. Suitable single-sided hook materials for the fastening components 82 or the mating fastening components 84 are available from Velcro Industries B.V., Amsterdam, Netherlands or affiliates thereof. In one embodiment, the outer cover material and/or the body side liner material may serve as a hook type fastener.

Figure 5:
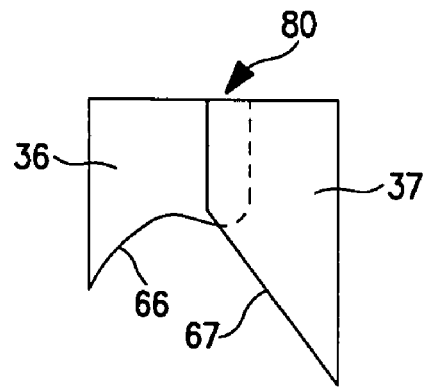
FIGS. 5–9 illustrate releasably engaged side panels in a fastened state.
Figure 8:
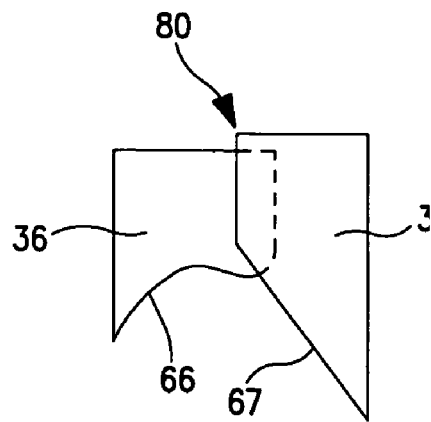
Figure 6:
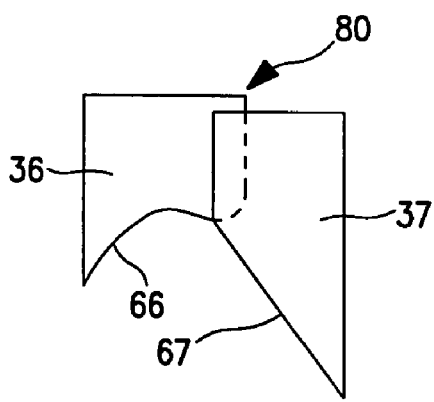
Figure 9:
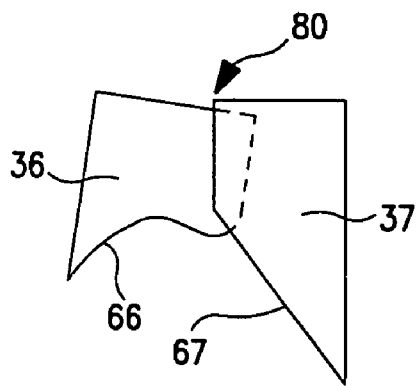
Figure 7:
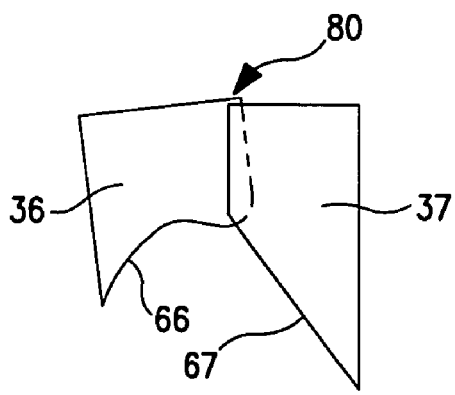

The front panel 36 may overlap the back panel 37, or vice-versa, with the fastening component 82 attached to an inner surface 62 of the front panel 36 and the mating fastening component 84 attached to an outer surface 64 of the back panel 37, or vice-versa. Additionally, the front panel 37 may have an S shape along a bottom edge 66, as shown in FIG. 5, to minimize any sharp corners at the leg opening that can result when a lap seam is formed. This S shape is particularly advantageous in designs having a higher leg cut since the back panel 37 has a relatively highly angled shape in such embodiments. Furthermore, the S shape also serves to minimize the size of any corners that result from process variability and/or user fastening variability. Examples of releasably engaged front and back panels that have undergone process and/or user fastening variability, yet have minimized sharp corners due to the S-shaped edge, are shown in FIGS. 6–9. In one embodiment in which the front panel 36 has an S-shaped bottom edge 66, the narrowest longitudinal dimension of the front panel 36 is narrower than the narrowest longitudinal dimension of the back panel 37.

The narrowest longitudinal dimension 56 of the side panels 34 may be located roughly mid-way between the front and back regions, for example at the side seam 54 in an embodiment wherein each side panel 34 includes a front panel 36 and a back panel 37 permanently bonded along a side seam 34, or may be located in the front region, such as on the front panel 36. The side panels 34, whether separately attached to the front and back regions or integral with the front and back regions, extend from the waist opening 50 to one of the leg openings 52, suitably having a continually decreasing length dimension moving in an outward transverse direction, as best shown in FIGS. 3 and 4, suitably in a curvilinear leg end edge 66 along a front portion of the side panel and either a curvilinear or linear leg end edge 67 along a back portion of the side panel.

The side panels 34 desirably include an elastic material capable of stretching in a direction generally parallel to the transverse axis 49 of the training pant 20. Suitable elastic materials, as well as processes of incorporating side panels into a training pant, are known to those skilled in the art, and are described, for example, in U.S. Pat. No. 4,940,464 issued Jul. 10, 1990 to Van Gompel et al., which is incorporated herein by reference.

The outer cover 40 suitably covers the front region 22, crotch region 26, and back region 24. In certain embodiments, the outer cover 40 may also cover, or form, the side panels 34 as well, creating an all-encompassing, one-piece garment exterior. The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

Necked-bonded laminates are particularly suitable for forming the outer cover 40. Necked-bonded laminates, in general, include at least one layer of necked or neckable material bonded to a stretchable or elastomeric layer. Necked-bonded laminates, and methods of making necked-bonded laminates, are taught, for example, in U.S. Pat. No. 5,910,224 to Morman, incorporated herein by reference.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Pliant Corporation of Schaumburg, Ill., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain non-breathable elastic films can also be used to make the outer cover 40. Examples of suitable non-breathable films can be made of styrene-ethylene-butylene-styrene or styrene-isoprene-styrene block copolymers, KRATON polymers from Kraton Polymers USLLC of Belpre, Ohio, U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the wearer's skin. Further, the body side liner 42 can be less hydrophilic than the absorbent assembly 44, to present a relatively dry surface to the wearer and permit liquid to readily penetrate through its thickness.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL™ N-62 available from available from Uniqema Inc., a division of ICI of New Castle, Del., U.S.A. and GLUCOPON™ 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include elastomeric materials, it can be desirable in some embodiments for the composite structure to be generally inelastic, where the outer cover, the body side liner and the absorbent assembly include materials that are generally not elastomeric.

The absorbent assembly 44 can be any structure which is generally compressible, conformable, non-irritating to the wearer's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The absorbent assembly 44 can have variable thickness, with greater thickness in target areas, such as in a central portion of the crotch region. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 can include an extremely thin absorbent composite material sold under the trade name NOVATHIN™ available from Rayonier Corporation located in Jessup, Ga., U.S.A., and/or an ultra-thin-absorbent (UTA) material including a mixture of SAP and pulp fiber. An example of a suitable UTA may include 3.7 grams (g) of FAVOR™ SXM 9543 SAP, available from Stockhausen GmbH & Co. KG located in Krefeld, Fed. Rep. of Germany, and 3.7 g of NB416 pulp fiber available from Weyerhauser located in Federal Way.

The absorbent assembly 44 can be contoured to fit the shape of the outer cover 40. In particular, when the outer cover 40 is a necked-bonded laminate or other stretchable or elastomeric material, the absorbent assembly 44 can be contoured to fit the shape of the stretchable outer cover, as shown in FIG. 4.

The chassis 32 can also incorporate other materials that are designed primarily to receive, temporarily store, and/or transport liquid along the mutually facing surface with the absorbent assembly 44, thereby maximizing the overall absorbent capacity of the absorbent assembly 44, if desired. One suitable material is referred to as a surge layer.

To further enhance containment and/or absorption of body exudates, the training pant 20 may include a front waist elastic member 68, a rear waist elastic member 70, and leg elastic members 72, as are known to those skilled in the art (FIG. 4). Alternatively, instead of separate, disconnected front and rear waist elastic members 68, 70, an all-encompassing waist elastic member 74 that fully encircles the waist opening 50 of the training pant 20 may be included in the pant. The waist elastic members 68, 70, 74 can be operatively joined to the outer cover 40 and/or body side liner 42 along the opposite waist edges 38 and 39, and can extend over part or all of the waist edges. The leg elastic members 72 are desirably operatively joined to the outer cover 40 and/or body side liner 42 along opposite side edges of the chassis 32 and positioned in the crotch region 26 of the training pant 20.

The waist elastic members 68, 70, 74 and the leg elastic members 72 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 72 include a plurality of dry-spun coalesced multifilament spandex elastomeric threads sold under the trade name LYCRA™ and available from E. I. DuPont de Nemours and Company, Wilmington, Del., U.S.A.

To enhance containment and/or absorption of any body exudates discharged from the wearer, the chassis 32 may include a pair of containment flaps 46 which are configured to provide a barrier to the transverse flow of body exudates. A flap elastic member 76 (FIG. 4) may be operatively joined with each containment flap 46 in any suitable manner as is well known in the art. The elasticized containment flaps 46 define an unattached edge 78 which assumes an upright, generally perpendicular configuration in at least the crotch region 26 of the training pant 20 to form a seal against the wearer's body. The containment flaps 46 can be located along the leg openings, encircling at least a portion of each of the leg openings. Suitable constructions and arrangements for the containment flaps 46 are generally well known to those skilled in the art.

The garments of the invention are designed to apply more pressure in a localized area to the body, thereby generating greater friction against the skin to hold the garment up. Greater friction between the garments of the invention and the wearer's body can overcome the friction between the garments and any outer garments that could otherwise pull the product down. Also, the garments may be easier to pull up compared to convention absorbent pant garments, since the high-cut side panels produce less drag against the wearer's legs.

The resulting absorbent pant garments of the invention provide a more secure, form-fitting product, compared to conventional absorbent pant garments, and have a styled appearance. In addition to providing these benefits, the high-cut side panels also provide an unprecedented level of discreetness, both in terms of less bulk as well as a reduction in the rustling and crinkling noises normally associated with absorbent pant garments. Furthermore, the high-cut side panels lie predominantly over low-motion areas of the body, i.e. the hips rather than the hips and thighs, thus reducing the likelihood of gapping when the wearer is in an unusual position or extreme motions.

As described herein, the various components of the absorbent garment can be assembled together employing various types of suitable attachment means, such as adhesive, sonic and thermal bonds or combinations thereof. The resulting product is an absorbent pant garment with high-cut side panels and having the comfort and style of underwear, particularly the style of female panties, with the absorbent and containment properties of a conventional absorbent pant garment.

Side Panel Dimensions Measurement Procedure

The measurements for the side panel width at the narrowest longitudinal dimension 56 and the width of the side panel along the side seam 54 can be measured by cutting the closed garment in half along a line parallel to the transverse axis 49 through the crotch region 26, then cutting the garment in half along a line parallel to longitudinal axis 48 thereby separating a right half of the garment from a left half, and laying one of the two halves of the garment out flat with the side seam 54 in a fastened position (if refastenable). The half of the garment is placed upon a flat solid surface, and the material of the side panels is gently spread (without stretching) to flatten the panels and remove any wrinkles or folds.

Figure 10:
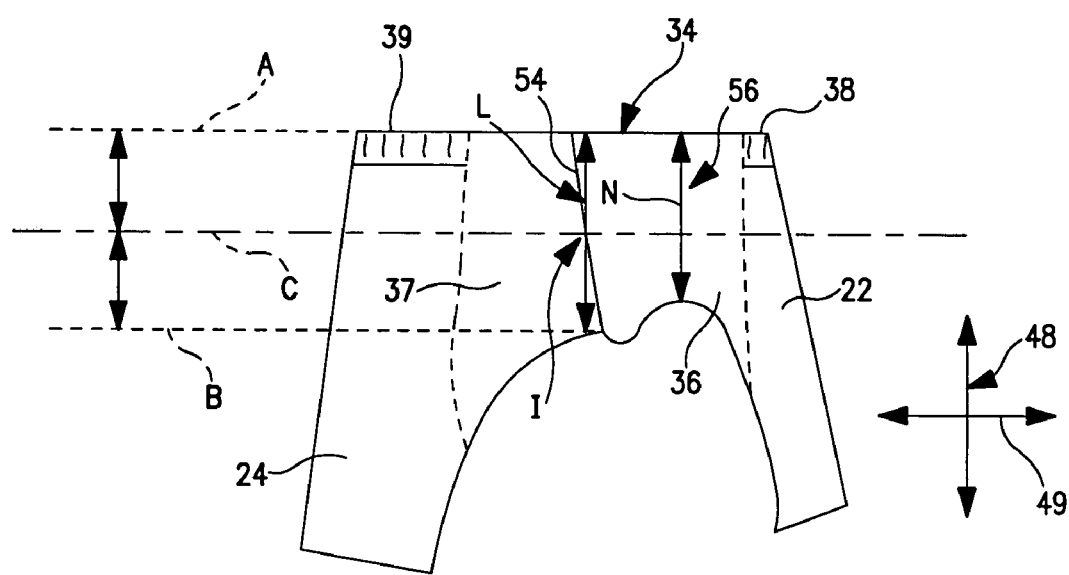
FIG. 10 illustrates a cut-apart pant garment with markings indicating the locations of dimensions to be measured.

When the garment is laid flat for measurement, the following dimensions, illustrated in FIG. 10, are defined:
  line A that is parallel to the transverse axis 49, and that is substantially aligned with the waist edge 38/39 of the garment;
  line B that is parallel to the transverse axis 49 and line A that passes through the point on the leg opening where the front panel 36 and the back panel 37 are joined to form the side seam 54
  line C that is parallel to both lines A and B, and lies halfway between A and B
    midpoint I is where line C intersects the seam at the midpoint of the seam, halfway between the waist opening and the leg opening
    longitudinal dimension L of seam 54 is the longitudinal width of the side panel at the center of the side seam and is determined by measuring the distance between the waist and leg edges defined along the line that passes through I and is perpendicular to the transverse axis 49
  line N is the side panel width at the narrowest longitudinal dimension 56 of the side panel and is measured parallel to the longitudinal axis 48 using a suitable scale Both the right and left side panel regions are measured on at least one, preferably at least three, representative products and the values are averaged to produce an average narrowest longitudinal dimension 56 of the front side panel 34 and an average width along the longitudinal width of the side panels at the center of the side seam 54. The ratio is calculated by dividing the narrowest longitudinal width 56 of the side panel 34 by the longitudinal width of the side panel at the center of the side seam 54.

Circumference Measurement Procedure

Figure 11:
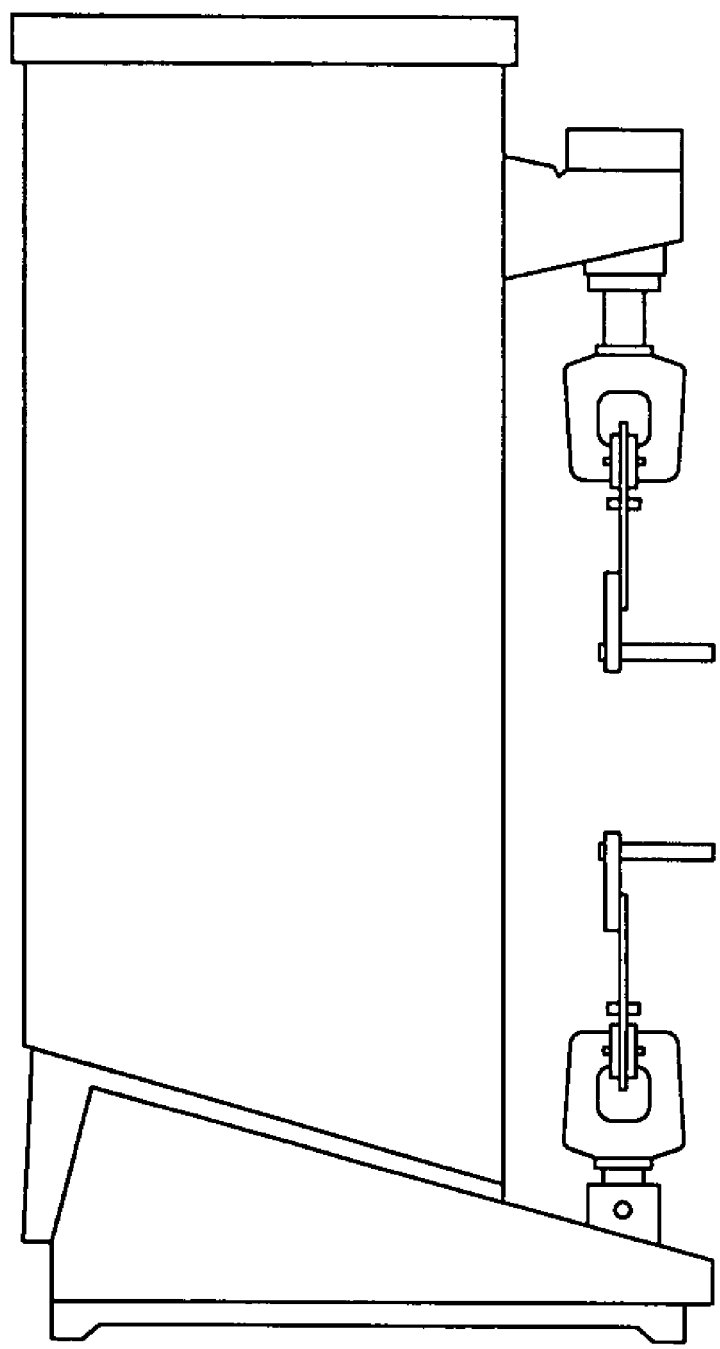
FIG. 11 illustrates a side view of a tensile tester used to measure a waist-to-leg circumference ratio of the pants shown in FIGS. 1 and 2.
Figure 12:
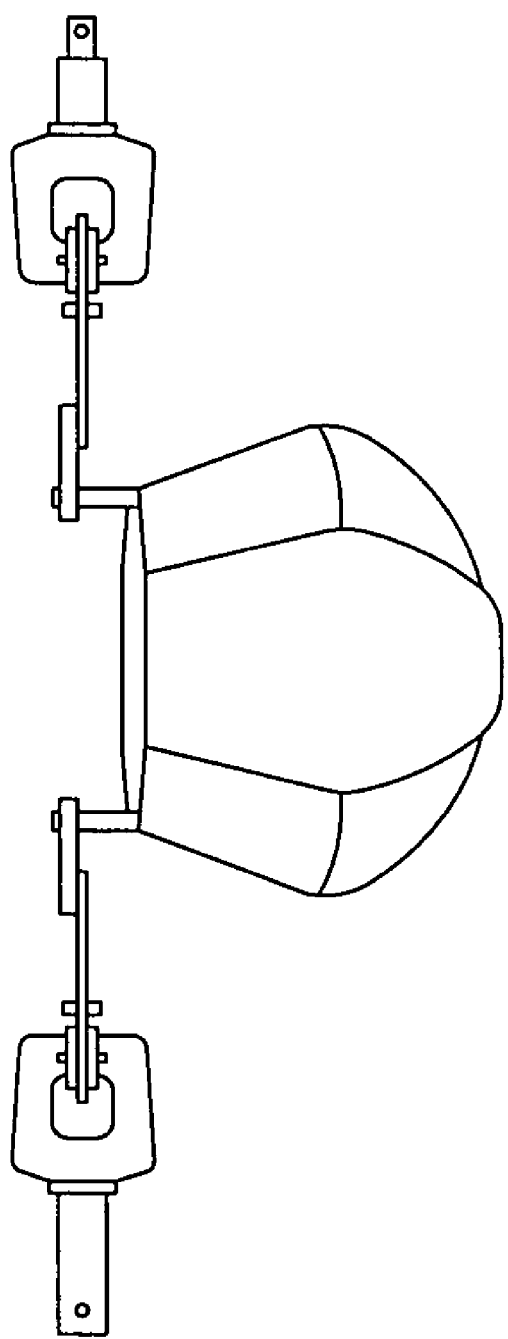
FIG. 12 illustrates a pant of the type shown in FIG. 1 disposed on the tensile tester to measure the waist circumference.
Figure 13:
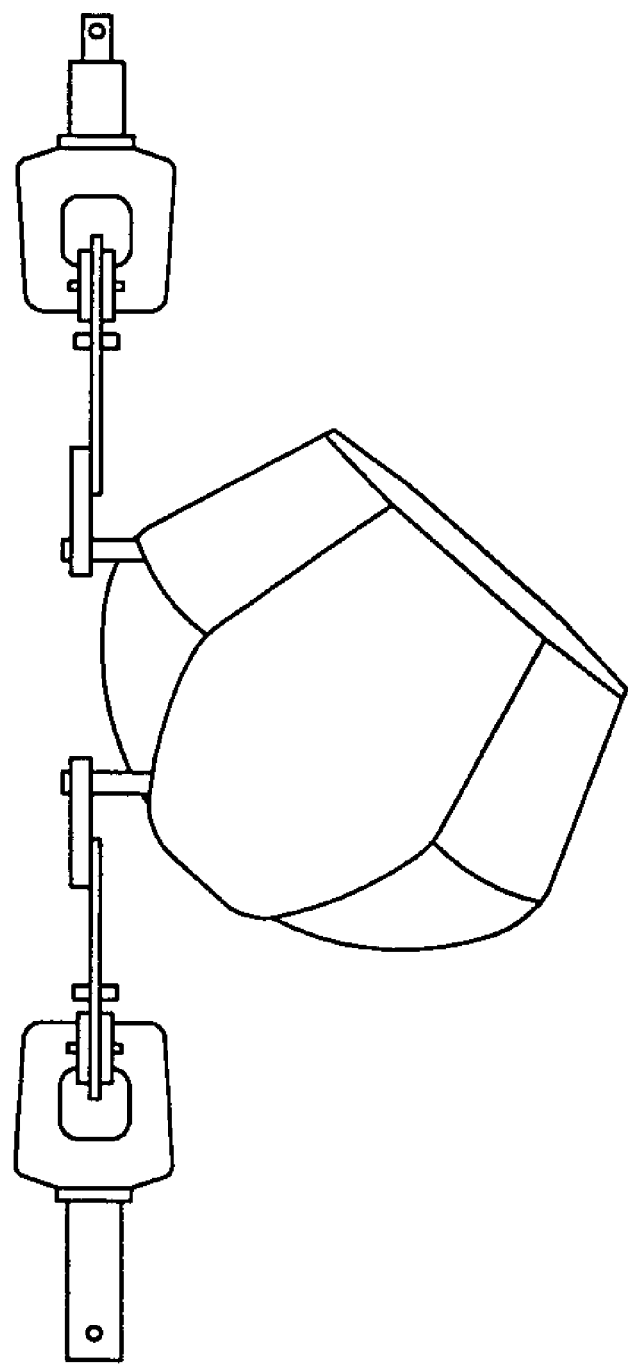
FIG. 13 illustrates a pant of the type shown in FIG. 1 disposed on the tensile tester to measure the leg circumference.

To measure the circumference of a waist opening or leg opening of a pant garment, a pant is placed on upper and lower pins of an MTS tensile tester model Synergie 200 Test Bed in position to measure the waist or leg gage length, as shown in FIGS. 11–13. The gage length is selected for the waist or leg opening of the pant being tested, so as to provide a tension of between 0 and 65 grams (g) when the pant is positioned for the test, prior to the start of the test. The term "tension" refers to the gram value measured by the load cells in the tensile tester.

The jaws are separated until a load of 70 grams of tension is attained, at which tension the gage length is recorded. The standard test is one cycle per pant. The circumference at the given tension, 70 g in this case, may be calculated using the gage length and the circumference value(s) for the upper and lower pins. Desirably, at least 3 pants are tested. The waist and leg circumference values at 70 g tension from each pant tested are averaged to obtain the average waist and leg circumferences. The sample products being tested can be randomized and separate samples can be used to test each product parameter, thus eliminating position interactions.

The leg-to-waist circumference ratio of the pant at 70 g loading (tension level) is the average leg circumference at that loading divided by the average waist circumference at the same loading. FIG. 11 illustrates a side view of a tensile tester used to measure leg-to-waist circumference ratios of pants according to the present invention. FIG. 12 illustrates a pant disposed on the tensile tester to measure the waist circumference. The leg circumference is measured similar to the waist circumference except the pins are inserted into one of the leg openings. Typically the top pin is inserted adjacent the side seam when the side seams are at or near the sides of the product. If there are no side seams or if the seams are not equidistant from the points where the longitudinal centerline passes through the front and back regions of the closed product, the top pin is placed in the center of the elastic area of the side panel as shown in FIG. 13. Then the bottom pin is placed in the crotch area in a way that equalizes the amount of material on each side of the leg opening between the two pins. The purpose of this is to ensure that the tension on both sides of the leg opening will be roughly equal when the gage length measurement is taken at the 70 g load.

The following is a list of apparatus and materials used in the Circumference Measurement Procedure:

Constant Rate of Extension (CRE) tensile tester: MTS tensile tester model Synergie 200 Test Bed; available from MTS® Systems Corporation, Research Triangle Park, N.C. USA.

Load cells: A suitable cell selected so the majority of the peak load values fall between the manufacturer's recommended ranges of load cell's full scale value; Model 100N available from MTS® Systems Corporation, Research Triangle Park, N.C. USA.

Operating software and data acquisition system: MTS TestWorks® for Windows software version 3.10; available from MTS® Systems Corporation, Research Triangle Park, N.C. USA.

Grips: pneumatic-action grips, top and bottom, identified as part number 2712-003 available from Instron Corporation, Canton, Mass. USA.

Grip faces: 25 by 75-mm (1 by 3-inch), suitable for holding pins.

Pins: rigid pins having a length of 6.3 centimeters (2.5 inch) and a knurled portion at one end for holding specimens, the knurled portion having an outside diameter of 6.4 millimeter (0.25 inch) and a length of 3.2 centimeters (1.25 inch).

Clip: 1.9 cm. wide by 0.95 cm. capacity (¾-inch wide by ⅜-inch capacity) binder clips; part no. BTM00251 available from BT Office Products, Milwaukee, Wis., USA.

Conditioning

Conduct test in standard ASTM laboratory conditions: atmosphere of 23±2° C. (73.4±3.6° F.) and 50±5% relative humidity. The products should be measured after they equilibrate to laboratory conditions.

Procedure

| Tensile Tester test conditions: | |
| --- | --- |
| Cross head speed: | 500 mm/min |
| Full scale load: | 4540 g |
| Gage length: | Appropriate starting gage length settings for both leg and waist are those that will generate initial loads of between 0 and 65 g in a previously untested product |
| Go to load (cycle trigger): | 70 g |
| Number of cycles: | 1 |
| Elongation stop: | 450 mm (200%) |
| Break sensitivity: | 75% |

A. Install pin assemblies as depicted in FIG. 11.
B. Using the tensile frame pushbutton controls for crosshead position, move pins so that the pant can be mounted on the pins without stretching the pant. Determine the gage length by measuring from the centerline of the first pin to the centerline of the second pin. Calibrate the software to this initial gage length.
C. Place the waist onto the knurled section of the top pin. Center one side of the pant on top of the pin. Use the binder clip to hold the pant at the waist opening in place on the pin; do not stretch the pant during application of the clip.
D. Click on ZERO to tare the load of the pant. Only tare the weight of the first pant for each sample population, not for each specimen.
E. Place the waist on the opposite side of the pant on the bottom pin. Adjust pant so both top and bottom pins are inserted 2.5 centimeters (1 inch) into the pant.
F. Using the tensile frame pushbutton controls for crosshead position, move pins apart until the load applied to the waist is between 0 and 65 g.
G. Click on RUN button. The test will start automatically.
H. When the test is done, click on either FILE to save the data and graphs or NEXT to save only the data.
I. Remove the sample from the pins.
J. Repeat steps B, C and E through I for each waist specimen until the testing is complete.
K. Using the tensile frame pushbutton controls for crosshead position, move pins toward one another so that the pant can be mounted on the pins without stretching the pant.
L. Place a fresh sample (not used for waist testing) onto the knurled section of the top pin by inserting the pin into a leg opening. Typically the top pin is inserted adjacent the side seam when the side seams are at or near the sides of the product. If there are no side seams or if the seams where they join the leg opening are closer to the front or back panel or region than the sides of the product, the top pin is placed in the center of the elastic area of the side panel as shown in FIG. 13. Use the binder clip to hold the pant in place on the pin; do not stretch the pant during application of the clip.
M. Click on ZERO to tare the load of the pant. Only tare the weight of the first pant for each sample population, not for each specimen.
N. Place the crotch area on the opposite side of the pant on the bottom pin. The product is placed on the pin in a way that equalizes the amount of material on each side of the leg opening between the two pins. The purpose of this is to ensure that the tension on both sides of the leg opening will be roughly equal when the gage length measurement is taken at the 70 g load. Then adjust pant so both top and bottom pins are inserted 2.5 centimeters (1 inch) into the pant.

O. Using the tensile frame pushbutton controls for crosshead position, move pins apart until the load applied to the hip section is between 0 and 65 g.
P. Click on RUN button. The test will start automatically.
Q. When the test is done, click on either FILE to save the data and graphs or NEXT to save only the data.
R. Remove the sample from the pins.
S. Repeat steps K, L and N through R for each leg and waist specimen until the testing is complete.

The circumference of a measured waist or leg section at 70 g tension may be calculated by multiplying the gage length at that tension by 2, and adding one half the circumference of the upper pin and one half the circumference of the lower pin. The leg-to-waist circumference ratio is calculated by dividing the average circumference of the leg at 70 g tension or load by the average circumference of the waist section at the same 70 g tension or load.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent pant garment, comprising:
an absorbent chassis defining a waist opening and first and second leg openings;
the absorbent chassis having a front region, a crotch region, and a back region, with two side panels each joining the front region and the back region, each of the side panels including a front panel and a back panel attached to one another along a side seam, wherein each side panel has a ratio of side panel width at a narrowest longitudinal dimension of the side panel divided by a width of the side panel along the side seam of less than about 0.7, and the narrowest longitudinal dimension of the side panel extends from the waist opening to a respective leg opening.

2. The absorbent pant garment of claim 1, wherein the ratio of the side panel width at the narrowest longitudinal dimension of the side panel divided by the width of the side panel along the side seam is less than about 0.6.

3. The absorbent pant garment of claim 1, wherein the ratio of the side panel width at the narrowest longitudinal dimension of the side panel divided by the width of the side panel along the side seam is less than about 0.5.

4. The absorbent pant garment of claim 1, wherein a ratio of a circumference of the first leg opening divided by a circumference of the waist opening is at least about 0.7.

5. The absorbent pant garment of claim 1, wherein a ratio of a circumference of the first leg opening divided by a circumference of the waist opening is at least about 0.8.

6. The absorbent pant garment of claim 1, wherein a ratio of a circumference of the first leg opening divided by a circumference of the waist opening is at least about 0.9.

7. The absorbent pant garment of claim 1, wherein the front panel and the back panel of each side panel are releasably engageable with one another along the side seam.

8. The absorbent pant garment of claim 7, wherein the narrowest longitudinal dimension of the side panel is located on the front panel.

9. The absorbent pant garment of claim 1, wherein the front panel and the back panel of each side panel are permanently bonded to one another along the side seam.

10. The absorbent pant garment of claim 9, wherein the narrowest longitudinal dimension of the side panel is located on the front panel.

11. An absorbent pant garment, comprising:
an absorbent chassis defining a waist opening and first and second leg openings;
the absorbent chassis having a front region, a crotch region, and a back region, with two side panels each joining the front region and the back region, each of the side panels including a front panel and a back panel refastenably attached to one another along a side seam, each of the front panels having an S shape along a bottom edge, wherein each side panel has a ratio of front panel width at a narrowest longitudinal dimension of the front panel divided by a width of the side panel along the side seam of less than about 0.7, and the narrowest longitudinal dimension of the side panel extends from the waist opening to a respective leg opening.

12. The absorbent pant garment of claim 11, wherein the ratio of the front panel width at the narrowest longitudinal dimension of the front panel divided by the width of the side panel along the side seam is less than about 0.6.

13. The absorbent pant garment of claim 11, wherein the ratio of the front panel width at the narrowest longitudinal dimension of the front panel divided by the width of the side panel along the side seam is less than about 0.5.

14. The absorbent pant garment of claim 11, wherein a ratio of a circumference of the first leg opening divided by a circumference of the waist opening is at least about 0.7.

15. The absorbent pant garment of claim 11, wherein a ratio of a circumference of the first leg opening divided by a circumference of the waist opening is at least about 0.8.

16. The absorbent pant garment of claim 11, wherein a ratio of a circumference of the first leg opening divided by a circumference of the waist opening is at least about 0.9.

17. The absorbent pant garment of claim 11, wherein the fastening system comprises a fastening component on an outer surface of each of the front side panels and a mating fastening component on an inner surface of each of the back side panels.

18. The absorbent pant garment of claim 11, further comprising a fastening component on an inner surface of each of the front side panels and a mating fastening component on an outer surface of each of the back side panels.

19. The absorbent pant garment of claim 11, wherein the narrowest longitudinal dimension of the front panel is narrower than a narrowest longitudinal dimension on the back side panel.

20. An absorbent pant garment, comprising:
an absorbent chassis defining a waist opening and first and second leg openings;
the absorbent chassis having a front region, a crotch region, a back region, and two side panels each joining the front region and the back region, each of the side panels including a front panel and a back panel attached to one another along a side seam, wherein each side panel has a ratio of side panel width at a narrowest longitudinal dimension of the side panel divided by a width of the side panel along the side seam of less than about 0.7,and a ratio of a circumference of the first leg opening divided by a circumference of the waist opening of at least about 0.8.

21. The absorbent pant garment of claim 20, wherein the ratio of the circumference of the first leg opening divided by the circumference of the waist opening is at least about 0.9.

22. The absorbent pant garment of claim 20, wherein a narrowest longitudinal dimension of the front panel is narrower than a narrowest longitudinal dimension of the back panel.

* * * * *